(12) United States Patent
Shin et al.

(10) Patent No.: US 11,452,483 B2
(45) Date of Patent: Sep. 27, 2022

(54) APPARATUS FOR ELIMINATING MOTION ARTIFACTS BY USING PPG SIGNAL AND METHOD THEREOF

(71) Applicant: SOONGSIL UNIVERSITY RESEARCH CONSORTIUM TECHNO-PARK, Seoul (KR)

(72) Inventors: Hyun-Chool Shin, Seoul (KR); Ji Hun An, Seoul (KR); Hee Mang Song, Suncheon-si (KR)

(73) Assignee: SOONGSIL UNIVERSITY RESEARCH CONSORTIUM TECHNO-PARK, Seoul (KR)

( * ) Notice: Subject to any disclaimer, the term of this patent is extended or adjusted under 35 U.S.C. 154(b) by 875 days.

(21) Appl. No.: 16/330,770

(22) PCT Filed: Jun. 23, 2017

(86) PCT No.: PCT/KR2017/006642
§ 371 (c)(1),
(2) Date: Mar. 6, 2019

(87) PCT Pub. No.: WO2018/048072
PCT Pub. Date: Mar. 15, 2018

(65) Prior Publication Data
US 2019/0192082 A1 Jun. 27, 2019

(30) Foreign Application Priority Data
Sep. 6, 2016 (KR) .................. 10-2016-0114398

(51) Int. Cl.
*A61B 5/00* (2006.01)
*A61B 5/11* (2006.01)
*A61B 5/024* (2006.01)

(52) U.S. Cl.
CPC .......... *A61B 5/721* (2013.01); *A61B 5/02416* (2013.01); *A61B 5/11* (2013.01);
(Continued)

(58) Field of Classification Search
CPC ..... A61B 5/02416; A61B 5/11; A61B 5/7257; A61B 5/721; A61B 5/7225
See application file for complete search history.

(56) References Cited

U.S. PATENT DOCUMENTS

2009/0024014 A1    1/2009   Sugo et al.
2015/0351646 A1* 12/2015   Cervini ............... A61B 5/7257
                                                                      600/479
(Continued)

FOREIGN PATENT DOCUMENTS

| JP | 2009-022484 A | 2/2009 |
| KR | 10-0462182 B1 | 12/2004 |
| KR | 10-2009-0096803 A | 9/2009 |

OTHER PUBLICATIONS

International Search Report for PCT/KR2017/006642 dated Sep. 11, 2017 from Korean Intellectual Property Office.

*Primary Examiner* — Michael J Dalbo
(74) *Attorney, Agent, or Firm* — Revolution IP, PLLC (57) ABSTRACT

The present invention relates to an apparatus for eliminating motion artifacts and a method thereof, and the method for eliminating motion artifacts includes steps of receiving a PPG signal and three-axis (X-axis, Y-axis, and Z-axis) acceleration signals measured from an examinee, extracting the PPG signal and the three-axis acceleration signals by a period of a predetermined unit of time and filtering the signals at a preset bandwidth, Fourier-transforming the PPG signal and the three-axis acceleration signals corresponding to the extracted period, arranging power spectra of the X-axis, Y-axis, and Z-axis in ascending order of value of average power spectrum by calculating an average power of (Continued)

each frequency domain of the three-axis accelerations, and extracting a final power spectrum of the PPG signal by sequentially eliminating power spectra of the X, Y, and Z-axis accelerations from the power spectrum of the PPG signal in an order of arrangement.

10 Claims, 6 Drawing Sheets

(52) U.S. Cl.
CPC .......... *A61B 5/7225* (2013.01); *A61B 5/7257* (2013.01); *A61B 2562/0219* (2013.01)

(56) References Cited

U.S. PATENT DOCUMENTS

| | | | |
|---|---|---|---|
| 2016/0051157 A1* | 2/2016 | Waydo | A61B 5/7246 600/479 |
| 2016/0051158 A1 | 2/2016 | Silva | |
| 2016/0089086 A1 | 3/2016 | Lin et al. | |
| 2016/0097716 A1* | 4/2016 | Gulati | A61B 5/1495 250/340 |
| 2016/0120477 A1* | 5/2016 | Takahashi | A61B 5/681 600/500 |
| 2017/0164847 A1* | 6/2017 | Pande | A61B 5/721 |

\* cited by examiner

APPARATUS FOR ELIMINATING MOTION ARTIFACTS BY USING PPG SIGNAL AND METHOD THEREOF

TECHNICAL FIELD

The present invention relates to an apparatus for eliminating motion artifacts and a method thereof, and more specifically, an apparatus for eliminating motion artifacts that uses a PPG signal, which effectively eliminates motion artifact components from the PPG signal using three-axis acceleration values, and a method thereof.

BACKGROUND ART

Recently, interest in health has increased, and thus, a study has been increasingly conducted to identify a health state of a wearer by attaching an apparatus or a sensor to a wearable device so as to detect a bio-signal.

The use of a wearable device has an advantage in that unreasonable physical activity can be prevented because a user can check his or her health state in real time while moving or exercising.

At this time, a PPG (Photoplethysmogram) signal can be used to measure a pulse wave of the user, and the PPG signal represents a change in volume of blood vessels by projecting an LED (Light Emitting Diode) onto the skin and using absorbance of the reflected light.

That is, a heart rate of the user can be estimated in real time from the PPG signal representing the change in volume of the blood vessels caused by contraction and relaxation of the heart.

However, in a case where the user moves, motion artifacts (MA) are included in the PPG signal acquired from the wearable device due to the movement, which makes the PPG signal susceptible to distortion. That is, motion artifacts interfere heart rate information of the PPG signal, and thereby, it is difficult to accurately estimate an actual heart rate.

In order to solve this problem, a study is being conducted to eliminate motion artifact components from the PPG signal, but it is difficult to accurately measure the pulse wave of a moving user in real life using a motion artifact elimination technique that is limited in a situation of low motion artifacts, and the motion artifact elimination technique performed in a situation where the motion artifacts are large uses a high resolution spectrum estimation, and thereby, it takes a long time and it is difficult to accurately measure the pulse wave in real time.

A technology of background of the present invention is disclosed in Korean Patent No. 10-0462182 (issued on Dec. 16, 2004).

DISCLOSURE

Technical Problem

An object of the present invention is to provide an apparatus for eliminating motion artifacts that uses a PPG signal, which effectively eliminates motion artifact components from the PPG signal using three-axis acceleration values, and a method thereof.

Technical Solution

According to an embodiment of the present invention for solving the technical problem, a method for eliminating motion artifacts using an apparatus for eliminating motion artifacts includes steps of receiving a PPG signal and three-axis (X-axis, Y-axis, and Z-axis) acceleration signals measured from an examinee, extracting the PPG signal and the three-axis acceleration signals by a period of a predetermined unit of time and filtering the signals at a preset bandwidth, Fourier-transforming the PPG signal and the three-axis acceleration signals corresponding to the extracted period to transform into a frequency domain, arranging power spectra of the X-axis, the Y-axis, and the Z-axis in ascending order of value of average power spectrum by calculating an average power of each frequency domain of the three-axis accelerations, and extracting a final power spectrum of the PPG signal by sequentially eliminating power spectra of the X-axis, Y-axis, and Z-axis accelerations from the power spectrum of the PPG signal in an order of arrangement.

The period may be extracted to overlap a previous period by a preset time, and the step of arranging the power spectra of the X-axis, the Y-axis, and the Z-axis may include steps of calculating an average value of the power spectrum of each of the X-axis, the Y-axis, and the Z-axis using a least square method, and arranging the power spectra of the X-axis, the Y-axis, and the Z-axis in an ascending order from a small spectrum having a small average value to a large spectrum.

The step of extracting the final power spectrum of the PPG signal may include steps of setting a first coefficient value of a power spectrum corresponding to a first axis having a smallest power spectrum among the X axis, the Y axis, and the Z axis, subtracting a value obtained by multiplying the spectrum of the first axis by the first coefficient value from a power spectrum of the PPG signal, setting a second coefficient value of a second axis having a second smallest power spectrum among the X-axis, the Y-axis, and the Z-axis using the power spectrum of the subtracted PPG signal, subtracting a value obtained by multiplying the spectrum of the second axis by the second coefficient value from the power spectrum of the subtracted PPG signal, setting a third coefficient value of a third axis having a largest power spectrum among the X axis, the Y-axis, and the Z-axis using the power spectrum of the subtracted PPG signal, and extracting a power spectrum ($P_i^4(f)$) by subtracting a value obtained by multiplying a spectrum of the third axis by the third coefficient value from the power spectrum of the subtracted PPG signal.

The first to third coefficient values ($C_k(i)$) may be set to satisfy a following condition $$c_k(i) = \operatorname*{argmin}_c \|P_i^k(f) - cA_i^k(f)\|$$

constrained to $$\left(\frac{1}{2}\max(P_i^k(\Delta f)) - cA_i^k(\Delta f)\right) \geq 0, (k = 1, 2, 3)$$

where $Pi^k(f)$ denotes a power spectrum of the PPG signal, c denotes a coefficient, $Ai^k(f)$ denotes power spectra of the three-axis accelerations, k denotes indices of the first to third axes corresponding to an arranged order, $\Delta f$ denotes a guard band using a heart rate estimated in the previous period.

The first to third coefficient values may be corrected by using the calculated coefficient ($c_k(i)$) and a coefficient ($\mu \bar{c}_k(i-1)$) of a previous period as represented by a following equation $$\bar{c}_k(i)=\mu\bar{c}_k(i-1)+(1-\mu)c_k(i)$$

where $\bar{c}_k(i)$ is first to third corrected coefficient values, and $\mu$ is a parameter used for an autoregressive model, and $\bar{c}_k(1)=\bar{c}_k(1)$ is set to an initial value.

The step of extracting the final power spectrum of the PPG signal may include a step of extracting a power spectrum ($\bar{P}_i(f)$) of a final PPG signal by using a power spectrum ($\bar{P}_{i-1}(f)$) of the final PPG signal extracted from a previous period and a power spectrum ($P_i^4(f)$) of a PPG signal obtained by subtracting a value obtained by multiplying a spectrum of the third axis by the third coefficient value, as represented by a following equation $$P_i^{k+1}(f)=P_i^k(f)-\bar{c}_k(i)A_i^k(f)$$

$$\bar{P}_i(f)=\epsilon\bar{P}_{i-1}(f)+(1-\epsilon)P_i^A(f)$$

where $P_i^{k+1}(f)$ denotes a power spectrum obtained by subtracting a power spectrum of an axis multiplied by a coefficient value from the power spectrum of the PPG signal, $\epsilon$ is a parameter for adjusting the sum of weighted values, and an initial value of the previous period is set to $\bar{P}_1(f)=P_1(f)$.

According to another embodiment of the present invention, an apparatus for eliminating motion artifacts includes a reception unit that receives a PPG signal and three-axis (X-axis, Y-axis, and Z-axis) acceleration signals measured from an examinee, a filter unit that extracts the PPG signal and the three-axis acceleration signals by a period of a predetermined unit of time and filtering the signals at a preset bandwidth, a transformation unit that Fourier-transforms the PPG signal and the three-axis acceleration signals corresponding to the extracted period to transform into a frequency domain, an arrangement unit that arranges power spectra of the X-axis, the Y-axis, and the Z-axis in ascending order of value of average power spectrum by calculating an average power of each frequency domain of the three-axis accelerations, and an extraction unit that extracts a final power spectrum of the PPG signal by sequentially eliminating power spectra of the X-axis, Y-axis, and Z-axis accelerations from the power spectrum of the PPG signal in an order of arrangement.

Advantageous Effects

According to the present invention, by removing the three-axis acceleration value gradually from the axis having the small average value in the PPG signal, it is possible to remove the motion artifacts component stably and efficiently.

In addition, according to the present invention, there is an advantage that the amount of calculation is simplified compared with the existing motion artifact elimination algorithm.

BEST MODE FOR INVENTION

Hereinafter, embodiments of the present invention will be described in detail with reference to the accompanying drawings such that a person skilled in the art to which the present invention belongs can perform easily the embodiments. The present invention can be embodied in many different forms and is not limited to the embodiments described herein. In order to clearly describe the present invention, parts not related to the description are omitted, and a similar unit is denoted by a similar reference numeral throughout the specification.

When it is described throughout the specification that a unit includes an element, it means that the unit can further include other elements, rather than excluding other elements unless specifically described otherwise.

Hereinafter, embodiments of the present invention will be described in detail with reference to the accompanying drawings such that a person skilled in the art to which the present invention belongs can easily perform the embodiments.

Figure 1:
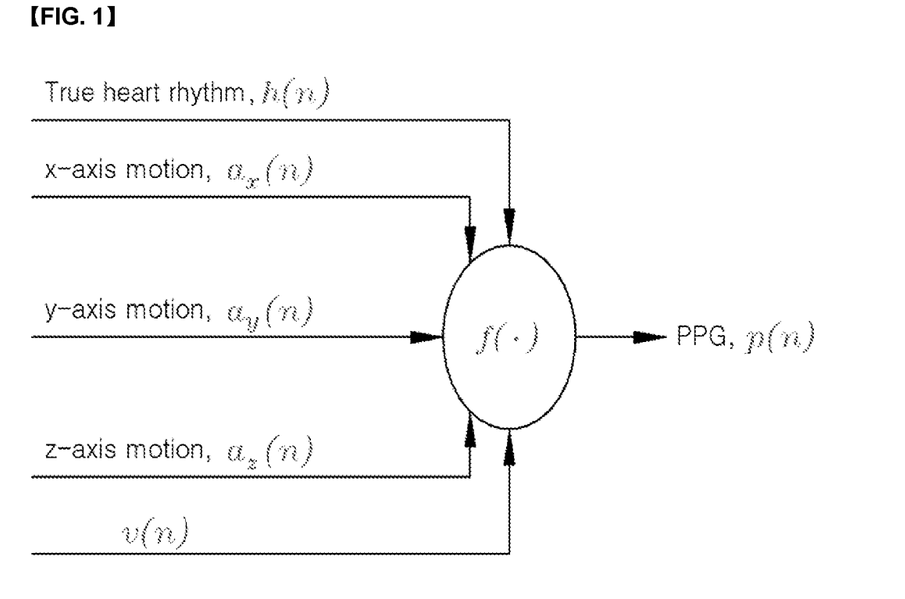
FIG. 1 is a diagram illustrating a PPG signal measured from an examinee according to an embodiment of the present invention.

FIG. 1 is a diagram illustrating a PPG signal measured from an examinee according to an embodiment of the present invention.

As illustrated in FIG. 1, the PPG signal measured from the examinee is configured by performing a non-linear combination of several signals.

That is, the PPG signal $p(n)$ includes pulse wave information (True heart rhythm, $h(n)$) capable of measuring a heart rate of the examinee, x-axis motion artifact $a_x(n)$, y-axis motion artifact $a_y(n)$, z-axis motion artifact $a_z(n)$, and noise $v(n)$ which is hard to be specified.

Here, since a motion artifact component is a noise generated due to movement of the examinee, the motion artifact component can be separately measured using three-axis acceleration values.

As such, since the motion artifact component included in the PPG signal causes the pulse wave information (True heart rhythm, $h(n)$) to be distorted so as to make the pulse wave hard to be measured through the PPG signal, in order to more accurately measure the pulse wave, the motion artifact elimination apparatus according to an embodiment of the present invention identifies a correlation between the PPG signal and the three-axis acceleration measurement value, gradually removes the three-axis acceleration measurement value from the PPG signal, and removes the motion artifacts.

Figure 2:
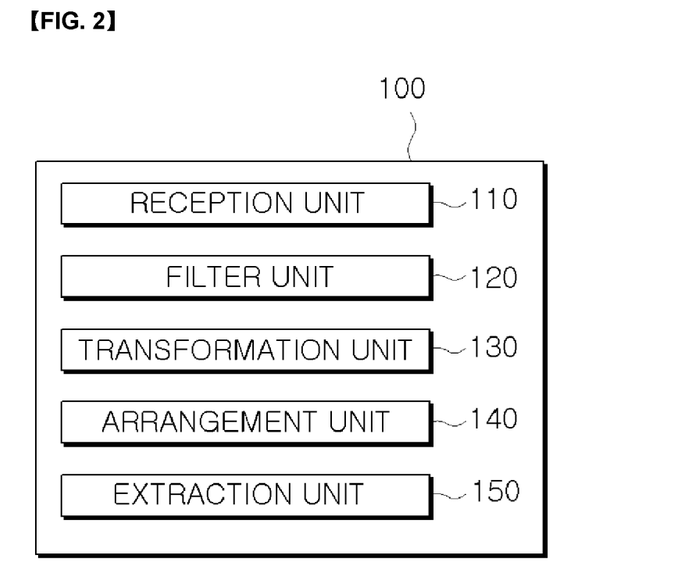
FIG. 2 is a configuration diagram illustrating a motion artifact elimination apparatus according to the embodiment of the present invention.

FIG. 2 is a configuration diagram illustrating a motion artifact elimination apparatus according to the embodiment of the present invention.

As illustrated in FIG. 2, a motion artifact elimination apparatus 100 according to the embodiment of the present invention includes a reception unit 110, a filter unit 120, a transformation unit 130, an arrangement unit 140, and an extraction unit 150.

The motion artifact elimination apparatus 100 according to the embodiment of the present invention may be embedded in an apparatus for measuring the PPG signal or a three-axis acceleration signals or an apparatus for providing pulse wave information of a user or may be a separate user terminal.

First, the reception unit 110 receives the PPG signal and the three-axis acceleration signals measured from the examinee. The reception unit 110 may be connected to a wearable apparatus worn on the body of the examinee or a server storing a measurement signal of the examinee wirelessly or by a wire to receive the PPG signal and the three-axis acceleration signals.

The filter unit 120 extracts the received PPG signal and three-axis acceleration signals by a period of a predetermined unit of time so as to overlap a previous period by a preset time.

In addition, the filter unit 120 may filter the PPG signal and the three-axis acceleration signals of the extracted period at a preset bandwidth corresponding to a pulse wave range measurable from the examinee. Here, the preset bandwidth can be individually set depending on an age, a sex, and physical characteristics of a person, and can be changed and set depending on a state of the examinee.

A sequence of a period extracting process and a bandwidth filtering process of the filter unit 120 is not fixed and can be changed by a user later.

In addition, the transformation unit 130 Fourier-transforms the PPG signal and the three-axis acceleration signals corresponding to the extracted period to transform a time domain into a frequency domain.

The arrangement unit 140 calculates an average power of each of frequency domains of the three-axis accelerations using the least square method. The arrangement unit 140 arranges power spectra of the X-axis, the Y-axis, and the Z-axis in ascending order of value of average power spectrum.

The extraction unit 150 sequentially removes the power spectra of the X-axis, Y-axis, and Z-axis accelerations in order of arrangement from the power spectrum of the PPG signal to extract the final power spectrum of the PPG signal.

Hereinafter, the method for eliminating motion artifacts according to an embodiment of the present invention will be described with reference to FIGS. 3 to 5.

Figure 3:
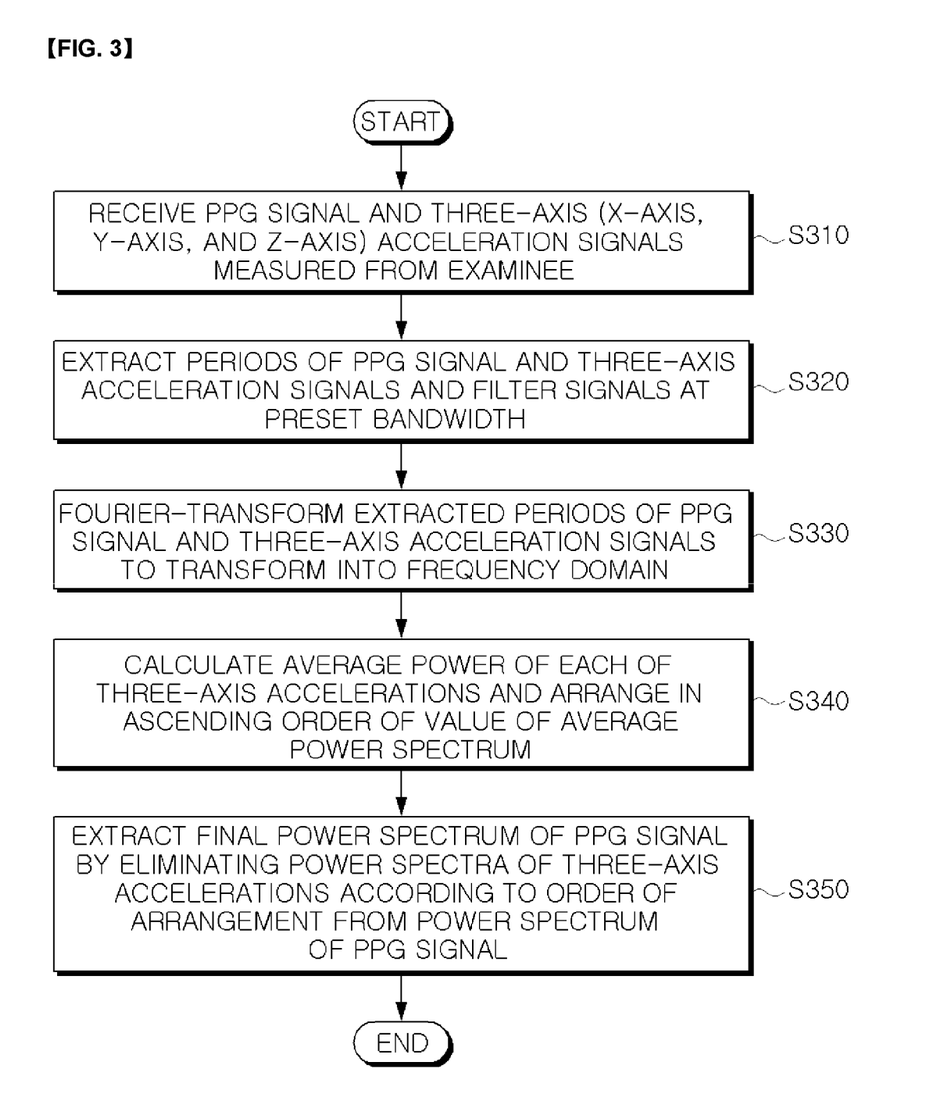
FIG. 3 is a flowchart illustrating a method for eliminating motion artifacts using the motion artifact elimination apparatus according to the embodiment of the present invention.
Figure 4:
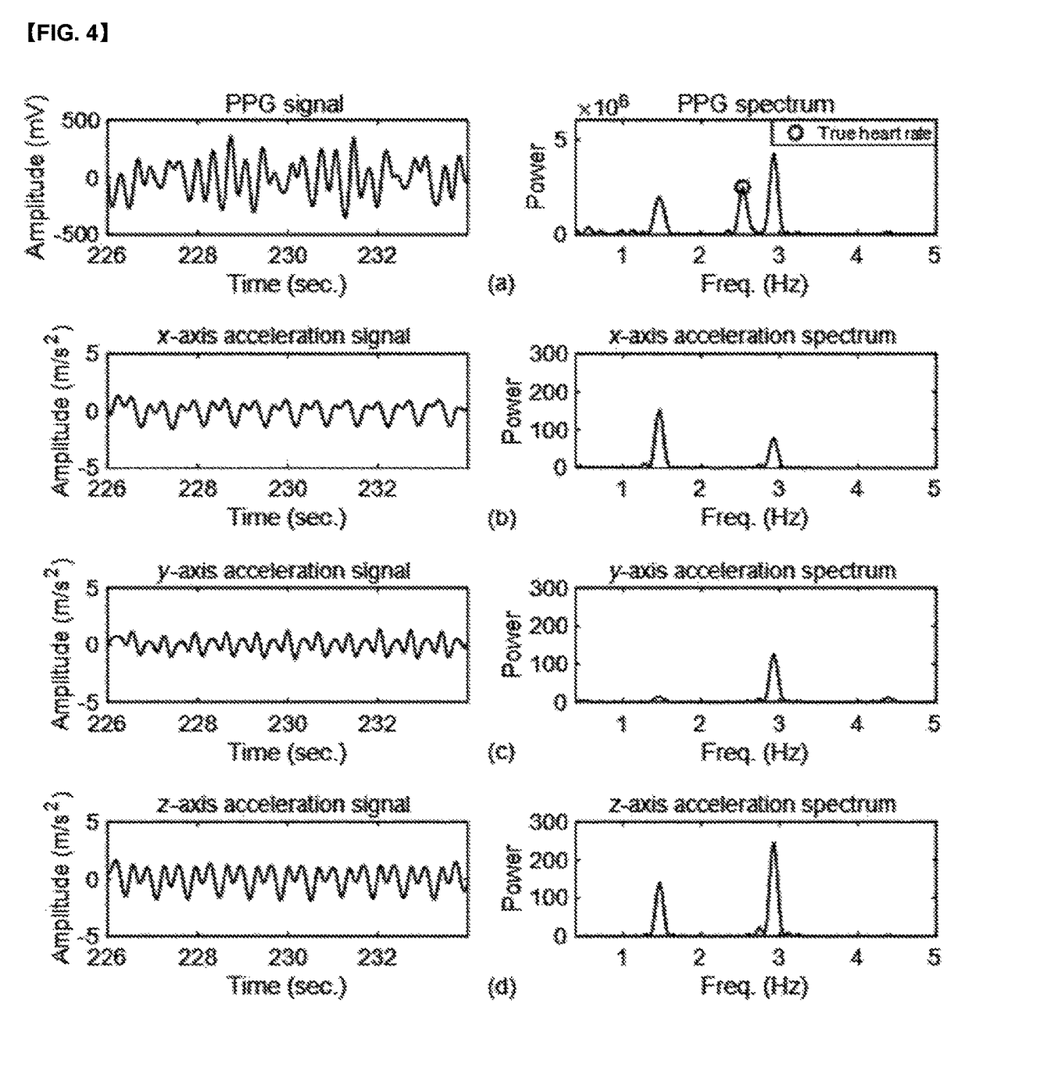
FIG. 4 illustrates graphs of a signal Fourier-transformed into a frequency domain by the motion artifact elimination apparatus according to the embodiment of the present invention.

FIG. 3 is a flowchart illustrating the method for eliminating motion artifacts using the motion artifact elimination apparatus according to the embodiment of the present invention, and FIG. 4 illustrates graphs of a signal Fourier-transformed into a frequency domain by the motion artifact elimination apparatus according to the embodiment of the present invention.

First, the reception unit 110 according to the embodiment of the present invention receives the PPG signal and three axis (X-axis, Y-axis, and Z-axis) acceleration signals measured from the examinee (S310).

Here, the PPG signal is a measured PPG signal having a non-linear combination of the PPG signal and noise and has a time domain value, and the three-axis acceleration signals indicates a value of each of the X-axis, Y-axis, and Z-axis along each axis.

The PPG signal and the three-axis acceleration signals can be received in real time from a wearable apparatus worn by the examinee or can be connected to a server or a database storing the measured signal to receive the PPG signal and the three-axis acceleration signals.

Next, the filter unit 120 extracts the PPG signal and the three-axis acceleration signals by a period of a predetermined unit of time and filters the PPG signal and the three-axis acceleration signals at a preset bandwidth (S320).

Here, the filter unit 120 may extract periods of the PPG signal and the three-axis acceleration signals so as to overlap the previous period by a preset time.

For example, if it is assumed that the predetermined unit of time is 8 seconds and the preset time is 6 seconds for the PPG signal and the three-axis acceleration signals measured for a total of 5 minutes, the filter unit 120 can extract a first period from 0 to 8 seconds in the whole measured period and extract a second period from 2 seconds to 10 seconds so as to overlap the first period by 6 seconds.

In addition, the filter unit 120 may generally filter the signal at a pulse wave bandwidth measurable from an adult. For example, if it is assumed that a pulse wave range measurable from the adult is 0.4 Hz to 5 Hz, the filter unit 120 can filter the PPG signal and the three-axis acceleration signals at a bandwidth of 0.4 Hz to 5 Hz.

At this time, the filter unit 120 can set a bandwidth to be filtered according to an age, a sex, and physical characteristics of an examinee in a personalized manner.

Then, the transformation unit 130 performs a fast Fourier transform of the PPG signal and the three-axis acceleration signals corresponding to the extracted period to transform into a frequency domain (S330).

It is difficult to intuitively identify influence of the three-axis acceleration signals on the PPG signal as the measured PPG signal and three-axis acceleration signals have larger motion artifacts in the time domain. Therefore, the transformation unit 130 performs a fast Fourier transform (FFT) so as to transform the PPG signal and the three-axis acceleration signals from the time domain into the frequency domain.

(a) of FIG. 4 is a graph of the PPG signal transformed from the time domain into the frequency domain. At this time, a circle portion indicates a true heart rate which is actually measured.

(b), (c), and (d) of FIG. 4 are graphs of the respective three-axis acceleration signals (x-axis, y-axis, and z-axis) transformed from the time domain into the frequency domain.

In a PPG spectrum in (a) of FIG. 4, it can be seen that a portion (remaining peak portion except for the circle portion) influenced by motion artifacts is larger than an actually measured pulse wave (the circle portion). That is, it can be seen that it is easy to determine the influence of spectrums of the three-axis accelerations on the actual PPG spectrum in the graph of the signal transformed into the frequency domain.

Therefore, the transformation unit 130 performs the fast Fourier transform of the PPG signal and the three-axis accelerations to transform into the frequency domain so as to easily determine a correlation between the PPG signal and the three-axis accelerations.

Next, the arrangement unit 140 calculates an average power of each of frequency domains of the three-axis accelerations and arranges power spectra of the X-axis, the Y-axis, and the Z-axis in ascending order of value of average power spectrum (S340).

That is, the arrangement unit 140 calculates the average power by using the least square method for the power spectra of the X-axis, the Y-axis, and the Z-axis which are transformed into the frequency domain. At this time, the arrangement unit 140 can calculate the average power of the power spectra using a method other than the least squares method.

The arrangement unit 140 can arrange the power spectra of the X-axis, the Y-axis, and the Z-axis in ascending order of value of average power spectrum. The arrangement unit 140 can arrange the axis having the smallest average power spectrum as a first axis, the axis having the second smallest average power spectrum as a second axis, and the axis having the largest average power spectrum as the third axis.

For example, if a magnitude of the power spectrum is calculated in the order of Z-axis>X-axis>Y-axis as illustrated in FIG. 4, arrangement is made such that the first axis is the Y-axis, the second axis is the X-axis, and the third axis is the Z-axis.

Next, the extraction unit 150 sequentially eliminates the power spectra of the X-axis, Y-axis, and Z-axis accelerations according in the order of arrangement from the power spectrum of the PPG signal to extract the final power spectrum of the PPG signal (S350).

That is, the extraction unit 150 can extract the final power spectrum by setting a coefficient value for each axis in the order in which the power spectra of the X-axis, Y-axis, and Z-axis accelerations are arranged, multiplying a corresponding coefficient value, and subtracting the value from the power spectrum of the PPG signal.

Hereinafter, a process of extracting the final power spectrum of the PPG signal using the extraction unit 150 of the motion artifacts elimination apparatus 100 will be described in detail with reference to FIG. 5.

Figure 5:
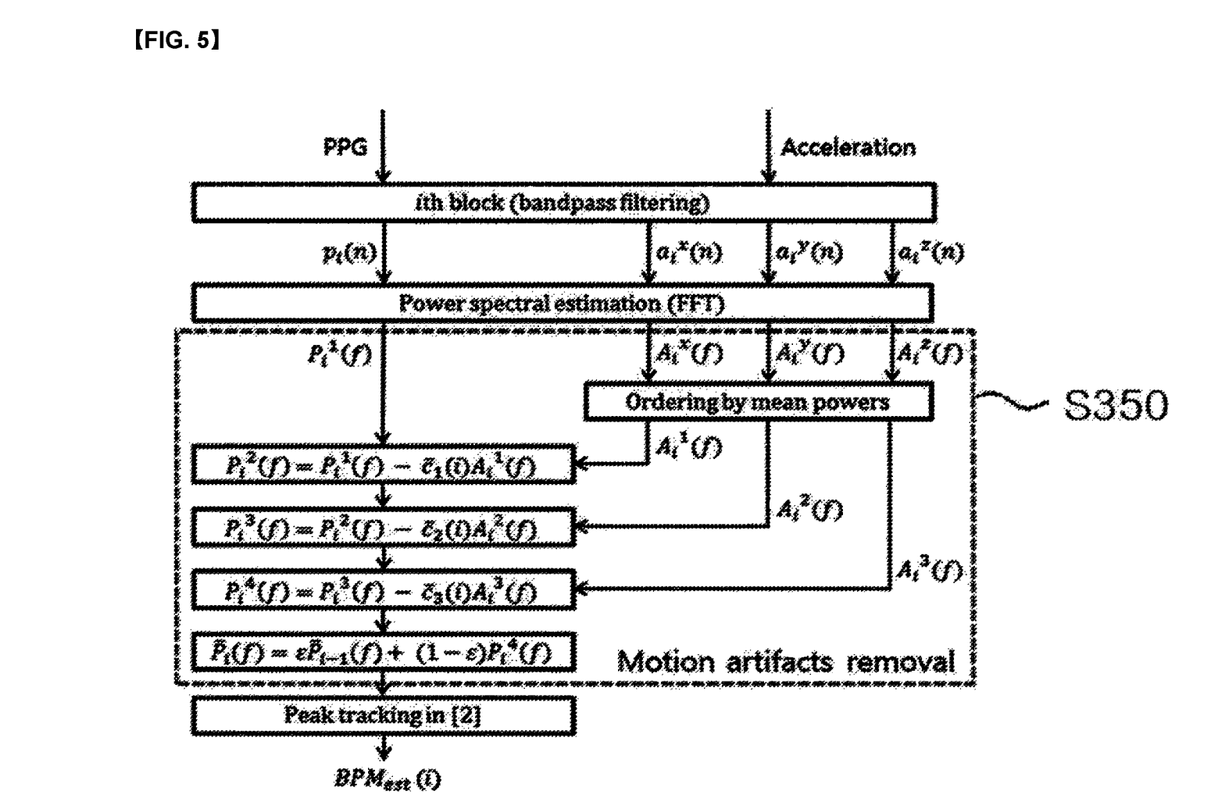
FIG. 5 is a diagram illustrating a process of eliminating motion artifacts from a PPG signal using the motion artifact elimination apparatus according to the embodiment of the present invention.

FIG. 5 is a diagram illustrating a process of eliminating motion artifacts from the PPG signal using the motion artifact elimination apparatus according to the embodiment of the present invention.

The extraction unit 150 of the motion artifact elimination apparatus 100 according to the embodiment of the present invention sets coefficient values for the respective axes so as to prevent a peripheral spectrum of the power spectrum representing the actual pulse wave from being completely eliminated when subtracting the power spectra of the three-axis accelerations from the power spectrum of the PPG signal and to eliminate the maximum motion artifacts at the same time.

That is, the extraction unit 150 can set each coefficient value for the power spectrum among the X-axis, Y-axis, and Z-axis using the PPG power spectrum. At this time, the motion artifact elimination apparatus 100 can set a coefficient value satisfying following Equation 1.

$$c_k(i) = \operatorname*{argmin}_{c} \|P_i^k(f) - cA_i^k(f)\| \quad \text{[Equation 1]}$$

constrained to $$\left(\frac{1}{2}\max(P_i^k(\Delta f)) - cA_i^k(\Delta f)\right) \geq 0, (k = 1, 2, 3)$$

Here, $P_i^k(f)$ denotes a power spectrum of the PPG signal, c denotes a coefficient, $A_i^k(f)$ denotes power spectra of three-axis accelerations, k denotes indices of the first to third axes corresponding to an arranged order, $\Delta f$ denotes a guard band using the heart rate estimated in the previous period, That is, as represented by Equation 1, the extraction unit 150 sets the coefficient value so as to be the smallest value by subtracting the power spectra of the three-axis accelerations obtained by multiplying the coefficient value from the power spectrum of the PPG signal.

However, in order to prevent the peripheral spectrum of the power spectrum representing the actual pulse wave from being completely eliminated, the extraction unit 150 can sets the coefficient value under the condition that a value greater than half is not removed from the power spectrum of the PPG signal having the largest value based on the pulse wave measured in the previous period.

The extraction unit 150 can correct the coefficient value by applying a coefficient $c_k(i)$ calculated through Equation 1 and a coefficient $\mu \bar{c}_k(i-1)$ of the previous period to following Equation 2.

$$\bar{c}_k(i) = \mu \bar{c}_k(i-1) + (1-\mu)c_k(i) \quad \text{[Equation 2]}$$

Here, $\bar{c}_k(i)$ is first to third corrected coefficient values, and $\mu$ is a parameter used for an autoregressive model, and $\bar{c}_k(1) = c_k(1)$ is set to an initial value.

That is, since there is an overlapping period between the previous period and the corresponding period, in order to prevent the coefficient values of the previous period and the corresponding period from rapidly changing, the coefficient value is corrected to be set within a predetermined range with the coefficient value of the previous period by using Equation 2.

Then, the extraction unit 150 multiplies the corresponding axis by the corrected coefficient value and subtract the multiplied value from the power spectrum of the PPG signal as represented by Equation 3.

$$P_i^{k+1}(f) = P_i^k(f) - \bar{c}_k(i)A_i^k(f)$$

As illustrated in FIG. 5, the extraction unit 150 sets the axis having the smallest value as a first axis $A_i^1(f)$, the axis having the second smallest value as a second axis $A_i^2(f)$, and the axis having the largest value as a third axis $A_i^3(f)$ according to a magnitude of the average power spectrum among the X-axis, Y-axis, and Z-axis, and hereinafter, for the sake of convenient description, it is assumed that the first axis is the Y-axis, the second axis is the X-axis, and the third axis is the Z-axis, as described above.

Then, the extraction unit 150 sets the first coefficient value ($\bar{c}_1(i)$) for the first axis (Y-axis) through Equation 1 and Equation 2 and extracts $P_i^2(f)$ by applying the set first coefficient value ($\bar{c}_1(i)$) to Equation 3 to subtracts from the power spectrum ($P_i^1(f)$) of the PPG signal.

The extraction unit 150 sets the second coefficient value ($\bar{c}_2(i)$) the second axis (X-axis) by applying the power spectrum ($P_i^2(f)$) of the PPG signal obtained by subtracting the power spectrum of the first axis (Y-axis) multiplied by the first coefficient value to Equation 1 and Equation 2. Then, the extraction unit 150 extracts ($P_i^3(f)$) by subtracting the power spectrum of the second axis (X-axis) multiplied by the second coefficient value ($\bar{c}_2(i)$) from the power spectrum ($P_i^2(f)$) of the PPG signal.

Then, the extraction unit 150 sets the third coefficient value ($\bar{c}_3(i)$) for the third axis (Z-axis) by applying the power spectrum ($P_i^3(f)$) of the PPG signal obtained by subtracting the power spectrum of the second axis multiplied by the second coefficient value to Equation 1 and Equation 2. Then, the extraction unit 150 extracts ($P_i^4(f)$) by subtracting the power spectrum of the third axis (Z-axis) multiplied by the third coefficient value ($\overline{c}_3(i)$) from the power spectrum ($P_i^3(f)$) of the PPG signal.

At this time, if the power spectrum of the PPG signal is smaller than a reference value, an accurate pulse wave measurement can be hard even if the power spectra of the three-axis acceleration signals are eliminated. Therefore, the extraction unit 150 uses the final power spectrum of the previous period when extracting the final power spectrum of the correspond period using characteristics of the continuous and overlapping periods.

The extraction unit 150 extracts the power spectrum ($\overline{P}_i(f)$) of the final PPG signal by applying the power spectrum ($P_i^4(f)$) of the PPG signal extracted by subtracting all the power spectra from the three-axis acceleration signals and the power spectrum ($\overline{P}_{i-1}(f)$) of the final PPG signal extracted in the previous period to following Equation 4.

$$\overline{P}_i(f)=\epsilon \overline{P}_{i-1}(f)+(1-\epsilon)P_i^4(f)$$ [Equation 4]

Here, $\epsilon$ is a parameter for adjusting the sum of weighted values, and an initial value of the previous period is set to $\overline{P}_1(f)=P_1(f)$.

In this way, the extraction unit 150 extracts the final power spectrum of the PPG signal of the corresponding period using the final power spectrum of the PPG signal of the previous period through Equation 4, thereby, being capable of reducing a pulse wave estimation error generated in a case where power of the actual pulse wave is small.

In this way, the extraction unit 150 sequentially eliminates the spectra of the three-axis accelerations multiplied by each coefficient value from the power spectrum of the PPG signal according to an arrangement order, and then, can extract the final power spectrum of the PPG signal of the corresponding period by using the final power spectrum value of the PPG signal of the previous period.

Figure 6:
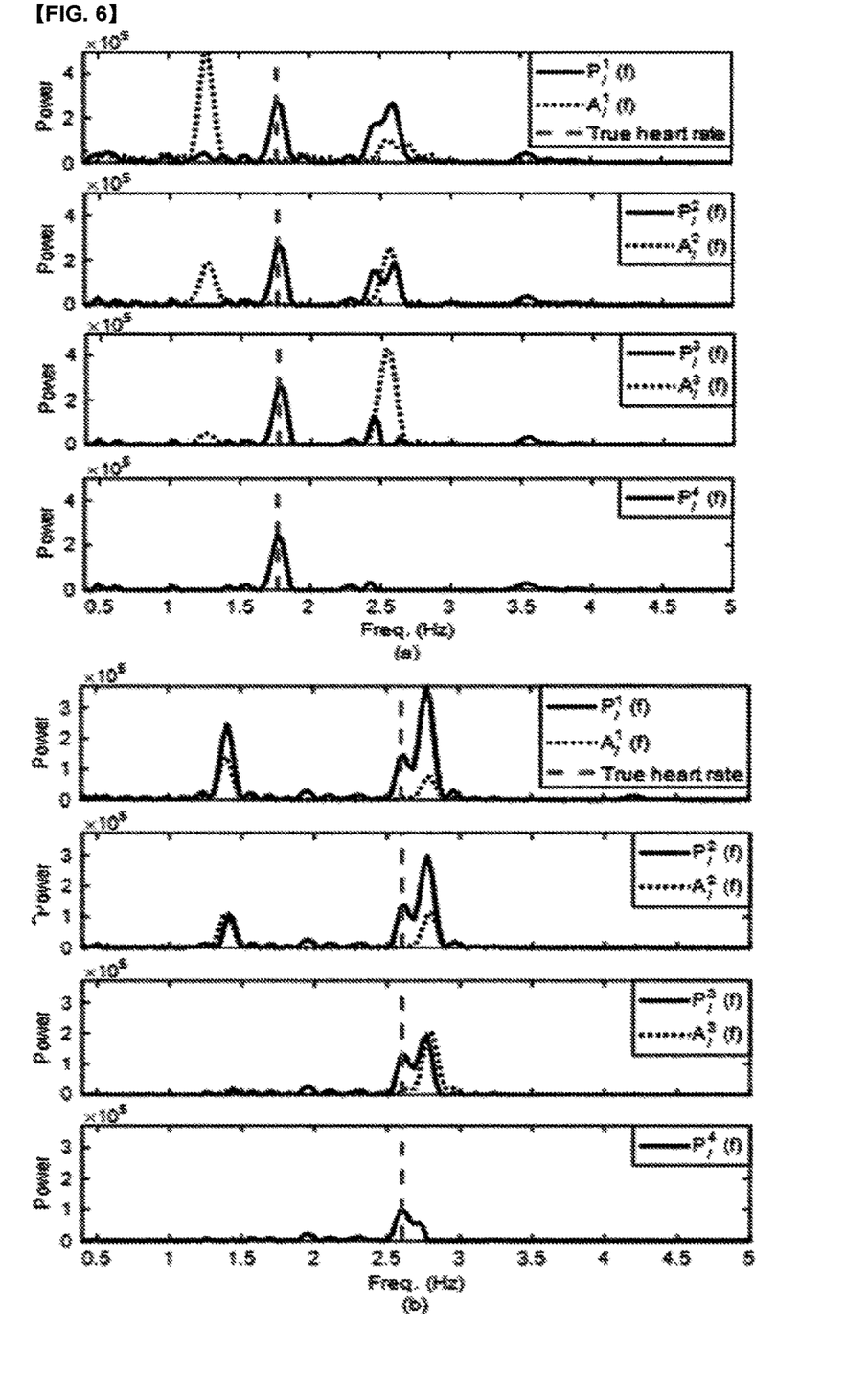
FIG. 6 illustrates graphs illustrating a process of estimating a final power spectrum by applying a method for eliminating motion artifacts according to an embodiment of the present invention.

FIG. 6 illustrates graphs illustrating a process of estimating the final power spectrum by applying a method for eliminating motion artifacts according to an embodiment of the present invention.

(a) of FIG. 6 illustrates the power spectrum of the PPG signal in a case where motion artifacts influence a frequency of the PPG signal which is different from a frequency of the PPG signal estimated as an actual pulse wave, and (b) of FIG. 6 illustrates the power spectrum of the PPG signal in a case where the motion artifacts influence the frequency of the PPG signal around the frequency of the PPG signal estimated as the actual pulse wave.

That is, in (a) of FIG. 6, it can be seen that the influence of the motion artifacts is large at a frequency different from the frequency (true heart rate) estimated as an actual pulse wave, and in (b) of FIG. 6, it can be seen that the influence of the motion artifacts is large at a frequency around the frequency (true heart rate) estimated as the actual pulse wave.

In (a) and (b) of FIG. 6, the frequency (true heart rate) estimated as an actual pulse wave is indicated by a dashed line, the graph illustrated by a solid line represents a power spectrum of the PPG signal, and a dotted line indicates the power spectrum of each axis multiplied by a coefficient.

In (a) and (b) of FIG. 6, each first graph represents the power spectrum (solid line: $P_i^1(f)$) of the PPG signal measured from an examinee and the power spectrum (dotted line: $A_i^1(f)$) of the first axis multiplied by the first coefficient value, and each second graph represents the power spectrum (solid line: $P_i^2(f)$) of the PPG signal from which the power spectrum ($A_i^1(f)$) of the first axis is eliminated and the power spectrum (dotted line: $A_i^2(f)$) of the second axis multiplied by the second coefficient value. In addition, each third graph represents the power spectrum (solid line: $A_i^2(f)$) of the PPG signal from which the power spectrum ($A_i^2(f)$) of the first axis is eliminated and the power spectrum (dotted line: $A_i^3(f)$) of the third axis multiplied by the third coefficient value, and each fourth graph represents the power spectrum ($P_i^4(f)$) of the PPG signal from which the power spectrum ($A_i^3(f)$) of the third axis is eliminated.

As can be seen from the first, second, and third graphs of (a) and (b) of FIG. 6, by gradually eliminating the power spectra of the three-axis accelerations from the power spectrum of the PPG signal, only the frequency (true heart rate) estimated as an actual pulse wave can be easily estimated, as illustrated in the fourth graph in (a) and (b) of FIG. 6.

That is, it can be seen that, in (a) and (b) of FIG. 6, the method for eliminating motion artifacts according to the embodiment of the present invention effectively eliminates the motion artifact component not only in a case where the motion artifact component influences a specific portion of the frequency domain of the PPG signal but also in all cases.

Figure 7:
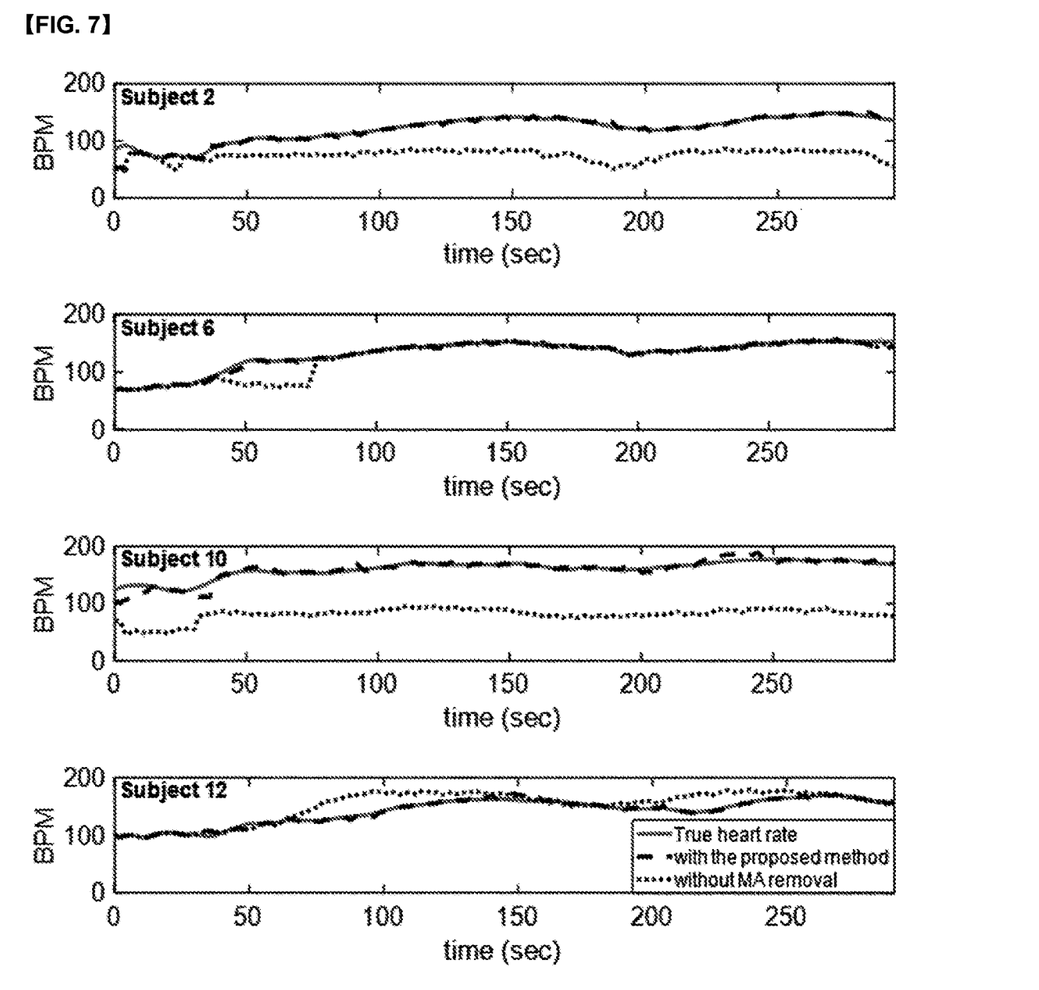
FIG. 7 illustrates graphs for comparing a pulse wave, an actual pulse wave, and a pulse wave from which motion artifacts are not eliminated, which are estimated by applying the method for eliminating the motion artifacts according to the embodiment of the present invention.

FIG. 7 illustrates graphs for comparing a pulse wave, an actual pulse wave, and a pulse wave from which the motion artifacts are not eliminated, which are estimated by applying the method for eliminating motion artifacts according to the embodiment of the present invention.

In FIG. 7, an individual heart rate was measured for each examinee with a sampling frequency of 125 Hz for each data for the PPG signal and the three-axis accelerations measured for examinees (subject 2, subject 6, subject 10, and subject 12) in exercise. At this time, the period is a period shifted by 2 seconds so as to overlap the previous period for 6 seconds by unit of time of 8 seconds, and a parameter Δf used when the coefficient value is set means a guard band which is [prevHR−12, . . . , prevHR+12] when a heart rate estimated in the previous period is referred to as prevHR. Each parameter is assumed to be μ=0.88 and ϵ=0.18.

FIG. 7 illustrates a result (with the proposed method) in which the heart rate is estimated by applying the method for eliminating motion artifacts according to the embodiment of the present invention, an actual heart rate (true heart rate), and a result (without MA removal) in which the heart rate is estimated from which motion artifacts are not eliminated.

Here, by using a method for estimating a heart rate using a PPG power spectrum, the heart rate can be estimated by setting the highest point exceeding a corresponding threshold as a heart rate candidate group in the spectrum from which motion artifacts are eliminated after the threshold is set, the heart rate can be estimated by using a probability density function (PDF) based on statistical information on the heart rate, or the heart rate can be estimated through a maximum likelihood (ML) among candidate groups.

In FIG. 7, the result of estimating the heart rate using the PPG spectrum from which the motion artifacts are not eliminated are greatly different from the actual heart rate. Meanwhile, it can be seen that the result of estimating the heart rate by applying the method for eliminating motion artifacts according to the embodiment of the present invention is little different illustrates from the actual heart rate.

That is, it can be seen from FIG. 7 that the method for eliminating motion artifacts according to the embodiment of the present invention is efficient in eliminating motion artifacts in the PPG power spectrum.

As described above, according to the embodiments of the present invention, by gradually eliminating three-axis acceleration values from an axis having a small average value in a PPG signal, motion artifacts can be eliminated stably and efficiently.

In addition, there is an advantage that the amount of calculation is simplified compared with the existing motion artifact elimination algorithm. While the present invention is described with reference to embodiments illustrated in the drawings, the embodiments are merely exemplary, and it will be understood by those skilled in the art that various modifications and equivalent embodiments can be made. Accordingly, the true scope of the present invention should be determined by the technical idea of the appended claims.

The invention claimed is:

1. A method for eliminating motion artifacts using an apparatus for eliminating motion artifacts comprising steps of:
   receiving a PPG signal and three-axis (X-axis, Y-axis, and Z-axis) acceleration signals measured from an examinee, wherein the receiving step includes measuring the PPG signal by projecting an LED (Light Emitting Diode) onto a skin of the examinee and using absorbance of the reflected light, using an accelerometer attached to the examinee to measure the three-axis acceleration signals, and estimating a heart rate from the PPG signal;
   extracting the PPG signal and the three-axis acceleration signals by a period of a predetermined unit of time and filtering the signals at a preset bandwidth;
   Fourier-transforming the PPG signal and the three-axis acceleration signals corresponding to the extracted period to transform into a frequency domain;
   arranging power spectra of the X-axis, the Y-axis, and the Z-axis in ascending order of value of average power spectrum by calculating an average power of each frequency domain of the three-axis accelerations; and
   extracting a final power spectrum of the PPG signal by sequentially eliminating power spectra of the X-axis, Y-axis, and Z-axis accelerations from the power spectrum of the PPG signal in an order of arrangement,
   wherein the step of extracting the final power spectrum of the PPG signal includes steps of
      setting a first coefficient value of a power spectrum corresponding to a first axis having a smallest power spectrum among the X axis, the Y axis, and the Z axis;
      a first subtracting a value obtained by multiplying the spectrum of the first axis by the first coefficient value from a power spectrum of the PPG signal;
      setting a second coefficient value of a second axis having a second smallest power spectrum among the X-axis, the Y-axis, and the Z-axis using the power spectrum of the first subtracted PPG signal;
      a second subtracting a value obtained by multiplying the spectrum of the second axis by the second coefficient value from the power spectrum of the first subtracted PPG signal;
      setting a third coefficient value of a third axis having a largest power spectrum among the X axis, the Y-axis, and the Z-axis using the power spectrum of the second subtracted PPG signal; and
      extracting a power spectrum ($P_i^4(f)$) by a third subtracting a value obtained by multiplying a spectrum of the third axis by the third coefficient value from the second power spectrum of the subtracted PPG signal.

2. The method for eliminating motion artifacts according to claim 1,
   wherein the period is extracted to overlap a previous period by a preset time, and
   wherein the step of arranging the power spectra of the X-axis, the Y-axis, and the Z-axis includes steps of
      calculating an average value of the power spectrum of each of the X-axis, the Y-axis, and the Z-axis using a least square method; and
      arranging the power spectra of the X-axis, the Y-axis, and the Z-axis in an ascending order from a small spectrum having a small average value to a large spectrum.

3. The method for eliminating motion artifacts according to claim 1,
   wherein the first to third coefficient values ($C_k(i)$) are set to satisfy a following condition $$c_k(i) = \underset{c}{\operatorname{argmin}} \|P_i^k(f) - cA_i^k(f)\|$$

constrained to $$\left(\frac{1}{2}\max(P_i^k(\Delta f)) - cA_i^k(\Delta f)\right) \geq 0, (k = 1, 2, 3)$$

where $P_i^k(f)$ denotes a power spectrum of the PPG signal, c denotes a coefficient, $A_i^k(f)$ denotes power spectra of the three-axis accelerations, k denotes indices of the first to third axes corresponding to an arranged order, $\Delta^f$ denotes a guard band using a heart rate estimated in the previous period.

4. The method for eliminating motion artifacts according to claim 3,
   wherein the first to third coefficient values are corrected by using the calculated coefficient ($c_k(i)$) and a coefficient ($\mu\bar{c}_k(i-1)$) of a previous period as represented by a following equation $$\bar{c}_k(i) = \mu\bar{c}_k(i-1) + (1-\mu)c_k(i)$$

where $\bar{c}_k(i)$ is first to third corrected coefficient values, and $\mu$ is a parameter used for an autoregressive model, and $\bar{c}_k(1) = \bar{c}_k(1)$ is set to an initial value.

5. The method for eliminating motion artifacts according to claim 1,
   wherein the step of extracting the final power spectrum of the PPG signal includes a step of
      extracting a power spectrum ($\bar{P}_i(f)$) of a final PPG signal by using a power spectrum ($\bar{P}_{i-1}(f)$) of the final PPG signal extracted from a previous period and a power spectrum ($P_i^4(f)$) of a PPG signal obtained by subtracting a value obtained by multiplying a spectrum of the third axis by the third coefficient value, as represented by a following equation $$P_i^{k+1}(f) = P_i^k(f) - \bar{c}_k(i)A_i^k(f)$$

$$\bar{P}_i(f) = \epsilon\bar{P}_{i-1}(f) + (1-\epsilon)P_i^4(f)$$

where $Pi^{k+1}(f)$ denotes a power spectrum obtained by subtracting a power spectrum of an axis multiplied by a coefficient value from the power spectrum of the PPG signal, $\epsilon$ is a parameter for adjusting the sum of weighted values, and an initial value of the previous period is set to $\bar{P}_1(f) = P_1(f)$.

6. An apparatus for eliminating motion artifacts comprising:
one or more units being configured and executed by a processor using algorithm, the algorithm which when executed, causing the processor to perform the one or more units, the one or more units comprising:
a reception unit that receives a PPG signal and three-axis (X-axis, Y-axis, and Z-axis) acceleration signals measured from an examinee, wherein the PPG signal is measured by projecting an LED (Light Emitting Diode) onto a skin of an examinee and using absorbance of the reflected light, and the three-axis acceleration signals are measured by using an accelerometer attached to the examinee to measure, wherein a heart rate is estimated from the PPG signal;
a filter unit that extracts the PPG signal and the three-axis acceleration signals by a period of a predetermined unit of time and filtering the signals at a preset bandwidth;
a transformation unit that Fourier-transforms the PPG signal and the three-axis acceleration signals corresponding to the extracted period to transform into a frequency domain;
an arrangement unit that arranges power spectra of the X-axis, the Y-axis, and the Z-axis in ascending order of value of average power spectrum by calculating an average power of each frequency domain of the three-axis accelerations; and
an extraction unit that extracts a final power spectrum of the PPG signal by sequentially eliminating power spectra of the X-axis, Y-axis, and Z-axis accelerations from the power spectrum of the PPG signal in an order of arrangement,
wherein the extraction unit
sets a first coefficient value of a power spectrum corresponding to a first axis having a smallest power spectrum among the X axis, the Y axis, and the Z axis,
first subtracts a value obtained by multiplying the spectrum of the first axis by the first coefficient value from a power spectrum of the PPG signal,
sets a second coefficient value of a second axis having a second smallest power spectrum among the X-axis, the Y-axis, and the Z-axis using the power spectrum of the first subtracted PPG signal,
second subtracts a value obtained by multiplying the spectrum of the second axis by the second coefficient value from the power spectrum of the first subtracted PPG signal,
sets a third coefficient value of a third axis having a largest power spectrum among the X axis, the Y-axis, and the Z-axis using the power spectrum of the second subtracted PPG signal, and
extracts a power spectrum ($P_i^4(f)$) by third subtracting a value obtained by multiplying a spectrum of the third axis by the third coefficient value from the power spectrum of the second subtracted PPG signal.

7. The apparatus for eliminating motion artifacts according to claim 6,
wherein the period is extracted to overlap a previous period by a preset time, and
wherein the arrangement unit calculates an average value of the power spectrum of each of the X-axis, the Y-axis, and the Z-axis using a least square method and arranges the power spectra of the X-axis, the Y-axis, and the Z-axis in an ascending order from a small spectrum having a small average value to a large spectrum.

8. The apparatus for eliminating motion artifacts according to claim 6,
wherein the first to third coefficient values ($C_k(i)$) are set to satisfy a following condition $$c_k(i) = \underset{c}{\mathrm{argmin}} \| P_i^k(f) - c A_i^k(f) \|$$

constrained to $$\left( \frac{1}{2} \max(P_i^k(\Delta f)) - c A_i^k(\Delta f) \right) \geq 0, (k = 1, 2, 3)$$

where $Pi^k(f)$ denotes a power spectrum of the PPG signal, c denotes a coefficient, $Ai^k(f)$ denotes power spectra of the three-axis accelerations, k denotes indices of the first to third axes corresponding to an arranged order, $\Delta^f$ denotes a guard band using a heart rate estimated in the previous period.

9. The apparatus for eliminating motion artifacts according to claim 8,
wherein the first to third coefficient values are corrected by using the calculated) coefficient ($c_k(i)$) and a coefficient ($\mu \bar{c}_k(i-1)$) of a previous period as represented by a following equation $$\bar{c}_k(i) = \mu \bar{c}_k(i-1) + (1-\mu) c_k(i)$$

where $\bar{c}_k(i)$ is first to third corrected coefficient values, and $\mu$ is a parameter used for an autoregressive model, and $\bar{c}_k(1) = \bar{c}_k(1)$ is set to an initial value.

10. The apparatus for eliminating motion artifacts according to claim 8,
wherein the extraction unit extracts a power spectrum ($\bar{P}_i(f)$) of a final PPG signal by using a power spectrum ($\bar{P}_{i-1}(f)$) of the final PPG signal extracted from a previous period and a power spectrum ($P_i^4(f)$) of a PPG signal obtained by subtracting a value obtained by multiplying a spectrum of the third axis by the third coefficient value, as represented by a following equation $$P_i^{k+1}(f) = P_i^k(f) - \bar{c}_k(i) A_i^k(f)$$

$$\bar{P}_i(f) = \epsilon \bar{P}_{i-1}(f) + (1-\epsilon) P_i^4(f)$$

where $Pi^{k+1}(f)$ denotes a power spectrum obtained by subtracting a power spectrum of an axis multiplied by a coefficient value from the power spectrum of the PPG signal, $\epsilon$ is a parameter for adjusting the sum of weighted values, and an initial value of the previous period is set to $\bar{P}_1(f) = P_1(f)$.

* * * * *